(12) United States Patent
Kim et al.

(10) Patent No.: US 7,719,002 B2
(45) Date of Patent: May 18, 2010

(54) PERFLUOROALKYLENEOXY GROUP-SUBSTITUTED PHENYLETHYLSILANE COMPOUND AND POLYMER THEREOF

(75) Inventors: Dong-Yu Kim, Gwangju (KR); Ji-Eun Ghim, Gwangju (KR); Chae-Min Chun, Gwangju (KR); Bo-Gyu Lim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 432 days.

(21) Appl. No.: 11/896,472

(22) Filed: Aug. 31, 2007

(65) Prior Publication Data
US 2008/0139766 A1 Jun. 12, 2008

(30) Foreign Application Priority Data
Sep. 28, 2006 (KR) .................. 10-2006-0094974

(51) Int. Cl.
*H01L 51/30* (2006.01)
(52) U.S. Cl. .......... 257/40; 257/E51.007; 257/E51.028
(58) Field of Classification Search .............. 257/40, 257/E51.004, E51.005, E51.006, E51.007, 257/E51.025, E51.027, E51.028
See application file for complete search history.

(56) References Cited

U.S. PATENT DOCUMENTS

| | | | | |
|---|---|---|---|---|
| 3,764,589 A | * | 10/1973 | Bond et al. | 525/326.5 |
| 4,028,483 A | * | 6/1977 | Bond et al. | 526/279 |
| 4,153,765 A | * | 5/1979 | Tsai | 525/370 |
| 4,537,983 A | * | 8/1985 | Seiler et al. | 556/479 |
| 4,839,452 A | * | 6/1989 | Kurita et al. | 528/15 |
| 5,130,214 A | * | 7/1992 | Yokoyama et al. | 430/49.1 |
| 5,262,260 A | * | 11/1993 | Yokoyama et al. | 430/58.75 |
| 5,523,441 A | * | 6/1996 | Kishita et al. | 556/413 |
| 6,573,196 B1 | * | 6/2003 | Gaillard et al. | 438/789 |
| 6,753,401 B1 | * | 6/2004 | Reddy et al. | 528/15 |
| 2008/0031830 A1 | * | 2/2008 | Eckert et al. | 424/49 |

FOREIGN PATENT DOCUMENTS

JP 2008081731 A * 4/2008

* cited by examiner

*Primary Examiner*—Anh Phung
*Assistant Examiner*—Michael Lulis
(74) *Attorney, Agent, or Firm*—Harness, Dickey & Pierce, P.L.C.

(57) ABSTRACT

Disclosed herein are a perfluoroalkyleneoxy group-substituted phenylethylsilane compound and a polymer thereof. The perfluoroalkyleneoxy group-substituted phenylethylsilane compound represented by Formula 1 has excellent thermal and chemical stability to be solution-processed in a monomer state, and the polymer prepared by thermally crosslinking the compound has a high resistance to organic solvents. Moreover, since an insulating layer prepared by applying the same shows improved thermal and physical properties, it is possible to manufacture organic thin-film transistors having a high on/off ratio in a simple process such as a photolithography for a large-size substrate:

[Formula 1]

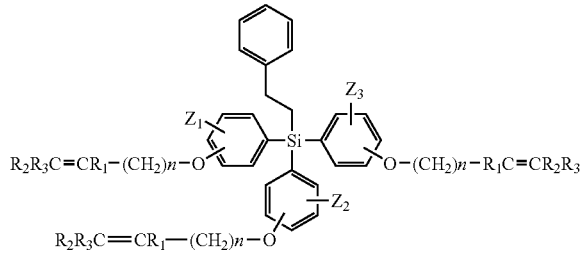

wherein $R_1$, $R_2$, $R_3$, $Z_1$, $Z_2$, $Z_3$, and n are the same as defined in the detailed description of the invention.

10 Claims, 9 Drawing Sheets

AFM images of croswslinking 3Si films (1μmX1μm)

Crosslinking film     Chloroform washing film     After PR pattern and e-beam deposition of electrode

PERFLUOROALKYLENEOXY GROUP-SUBSTITUTED PHENYLETHYLSILANE COMPOUND AND POLYMER THEREOF

CROSS-REFERENCE TO RELATED APPLICATION

This application claims the benefit of Korean Patent Application No. 10-2006-0094974, filed on 28, Sep. 2006, the entire disclosure of which is hereby incorporated by reference.

BACKGROUND OF THE INVENTION

1. Field of the Invention

The present invention relates to a perfluoroalkyleneoxy group-substituted phenylethylsilane compound and a polymer thereof and, more particularly, to a perfluoroalkyleneoxy group-substituted phenylethylsilane compound having excellent thermal and chemical stability to be solution-processed in a monomer state, a polymer prepared by thermal polymerization and having a high resistance to organic solvents, and uses thereof.

2. Description of Related Art

It is expected that an electronic circuit board that can be readily manufactured at low cost, not broken by impact but easily bent or folded, will become an essential element in the electronics industry in the future. Accordingly, the development of organic transistors that can meet such requirements has attracted much attention.

The organic transistors can be effectively used in many cases where there is a necessity to form organic elements on a wide area, where a lower processing temperature is required, where bendability is required, especially, where a low-cost process is required; however, it cannot be applied to an element, in which silicon Si, germanium Ge, and the like are employed, requiring a high speed operation due to low charge mobility in terms of characteristics of organic semiconductors.

A transistor element having excellent performance requires high on/off ratio and charge mobility. Moreover, the formation of thin film layer should be available at low temperature. This is because that it is difficult to increase the processing temperature since the glass transition temperature is very low (around 250° C. in case of polyimide) in terms of characteristics of plastic substrates. Moreover, a low current leakage is essential in terms of reliability.

Meanwhile, since a bottom-contact organic thin-film transistor prevents an organic semiconductor polymer from being contaminated in a patterning process, compared with a top-contact organic thin-film transistor, it does not deteriorate the element performance. Accordingly, a development of the bottom-contact organic thin-film transistor is required to fabricate a large-size element and thereby a development of a gate insulating material having excellent solvent resistance is necessary.

However, polymer insulating materials developed so far have a problem in that the on/off ratio is low. Accordingly, it is necessary to develop a new organic material meeting the requirements of the above-described organic thin-film transistor.

As a result of intensive studies to solve the above-described problems, the inventors of the present invention have found that a perfluoroalkyleneoxy group-substituted phenylethylsilane compound can be solution-processed in a monomer state since it has a phenethyl group, a polymerization reaction occurs based on a perfluorocyclobutene (PFCB) during the polymerization of monomers if heat is applied at a temperature below about 200° C., and the thus obtained polymer shows a high resistance to organic solvents, and completed the present invention.

Since the perfluoroalkyleneoxy group-substituted phenylethylsilane compound of the present invention has a high resistance to organic solvents, it is possible to apply a solution process to the compound. Moreover, it has been ascertained that the polymer obtained by thermal polymerization has a high resistance to organic solvents with excellent thermal and chemical stability. Furthermore, it has been found that, if the perfluoroalkyleneoxy group-substituted phenylethylsilane compound and the polymer thereof are applied to an insulating layer, the solution process can be employed due to the above-described characteristics. Especially, it has been also found that, if used as a gate insulating material for organic thin-film transistors, the perfluoroalkyleneoxy group-substituted phenylethylsilane compound and the polymer thereof have excellent thermal and physical resistance and thereby a method of manufacturing a large-size element can be applied using a photolithography process. In addition, it has been confirmed that the organic thin-film transistor in which the gate insulating material is used shows a high on/off ratio.

SUMMARY OF THE INVENTION

Accordingly, an object of the present invention is to provide a novel perfluoroalkyleneoxy group-substituted phenylethylsilane compound represented by Formula 1.

[Formula 1]

wherein $R_1$, $R_2$ and $R_3$ are the same or different, independently selected from the group consisting of a $C_1$-$C_4$ alkyl group and a $C_1$-$C_4$ fluoroalkyl group substituted with 1 to 6 fluoro atoms, and at least one fluoro atom or fluoroalkyl group; $Z_1$, $Z_2$ and $Z_3$ are the same or different and independently selected from the group consisting of a hydrogen atom and a $C_1$-$C_4$ alkyl group; and n is 0, 1, 2 or 3.

Moreover, the present invention provides a polymer prepared by polymerizing the perfluoroalkyleneoxy group-substituted phenylethylsilane compound.

Furthermore, the present invention includes an insulating layer using the perfluoroalkyleneoxy group-substituted phenylethylsilane compound and the polymer thereof.

In addition, the present invention includes a gate insulating material for organic thin-film transistors using the perfluoroalkyleneoxy group-substituted phenylethylsilane compound and the polymer thereof.

DETAILED DESCRIPTION OF THE INVENTION

Hereinafter, the present invention will be described with reference to the accompanying drawings.

The present invention provides a novel perfluoroalkyleneoxy group-substituted phenylethylsilane compound having excellent thermal and chemical stability. If the novel compound prepared in accordance with the present invention is used as a gate insulating material for organic thin-film transistors, it is possible to perform a spin coating process due to a high resistance to organic solvents. Moreover, with excellent thermal and physical resistance to organic solvents, it is possible to employ a method of manufacturing a large-size element using a photolithography process due to the excellent thermal and physical resistance of the novel compound. Furthermore, it can be expected that the thus fabricated organic thin-film transistor shows a high on/off ratio.

Since the perfluoroalkyleneoxy group in the perfluoroalkyleneoxy group-substituted phenylethylsilane compound represented by Formula 1 is a functional group required for the formation of a film by thermal crosslinking, at least one perfluoroalkyleneoxy group should be substituted in the structural formula. That is, at least one of the $R_1$, $R_2$ and $R_3$ should be a fluoro atom and the compound may be a compound represented by the following Formula 1a:

[Formula 1a]

The present invention includes a perfluoropolymer prepared by polymerizing the perfluoroalkyleneoxy group-substituted phenylethylsilane compound represented by Formula 1. The perfluoropolymer is cyclodimerized by thermal crosslinking to form a film.

That is, the present invention includes a perfluoropolymer having a repeating unit structure represented by the following Formula 2:

[Formula 2]

wherein $R_1$, $R_2$, $R_3$, $Z_1$, $Z_2$, $Z_3$, and n are the same as defined above in Formula 1.

More preferably, the present invention includes a perfluoropolymer having a repeating unit structure represented by the following Formula 2a:

[Formula 2a]

wherein $R_1$, $R_2$ and $R_3$ are the same as defined above in Formula 1.

The above polymer has excellent resistance to organic solvents and thereby a film prepared using the above polymer is not dissolved in organic solvents. Accordingly, a solution process such as spin coating and the like can be employed to facilitate the manufacturing process of the films. Especially, if the above polymer is used as a raw material for an insulating layer, it is possible to employ the solution process, thus providing advantages in view of the manufacturing process.

Moreover, the present invention includes a gate insulating material for organic thin-film transistors in which the polymer of Formula 2 prepared by polymerizing the compound of Formula 1 is introduced. That is, since the above polymer of Formula 2 has a high resistance to organic solvents and excellent thermal and physical stability, it is very advantageous if a gate insulating material for organic thin-film transistor is prepared using the polymer of Formula 2.

The gate insulating material may be prepared by coating a solution, in which the compound of Formula 1 is dissolved as a monomer, on a substrate, and then drying and heat-treating the resulting substrate.

It is preferable that the heat treatment be performed in the temperature range from 150° C. to 250° C. to increase the degree of polymerization. Moreover, it is more preferable that the heat treatment be carried out under vacuum conditions or in the presence of an inert gas such as nitrogen, argon, etc. commonly used in the art.

The present invention includes an organic thin-film transistor into which the gate insulating material is introduced.

Especially, the gate insulating material may be formed on the top (top gate) or on the bottom (bottom gate) of an organic semiconductor layer constituting an organic thin-film transistor.

In more detail, the present invention includes a bottom-contact organic thin-film transistor comprising a substrate, a gate insulating material layer formed on the substrate and including the perfluoropolymer of Formula 2, source/drain electrodes formed on the gate insulating material layer, and a semiconductor layer formed on the gate insulating material layer and including a channel layer formed over the source/drain electrodes and therebetween.

Moreover, the present invention includes a top-contact organic thin-film transistor comprising a substrate, source/drain electrodes formed on the substrate, a semiconductor layer formed on the substrate and including a channel layer formed over the source/drain electrodes and therebetween, and a gate insulating material layer formed on the semiconductor layer and including the perfluoropolymer of Formula 2.

A substrate commonly used in the art may be used as the substrate and, for example, a silicon wafer substrate, an indium tin oxide (ITO) substrate, and the like may be used; however, the present invention is not limited thereto.

As a metal thin film constituting the source/drain electrodes, a metal for electrodes or a conductive polymer commonly used in the art may be used. In more detail, the metal for electrodes or conductive polymer may include aurum (Au), argentum (Ag), copper (Cu), chromium (Cr), platinum (Pt), etc.

The semiconductor layer used as a channel of an organic field effect transistor (FET) may include an organic semiconductor material such as a small-molecule or polymer material commonly used in the art. In more detail, small molecules including pentacene and the like, and polymers including poly(3-hexylthiophene) and the like may be used.

A method of manufacturing an organic thin-film transistor, into which the gate insulating material including the perfluoroalkyleneoxy group-substituted phenylethylsilane compound of Formula 1 in accordance with the present invention is introduced, will be described as follows.

Figure 6:
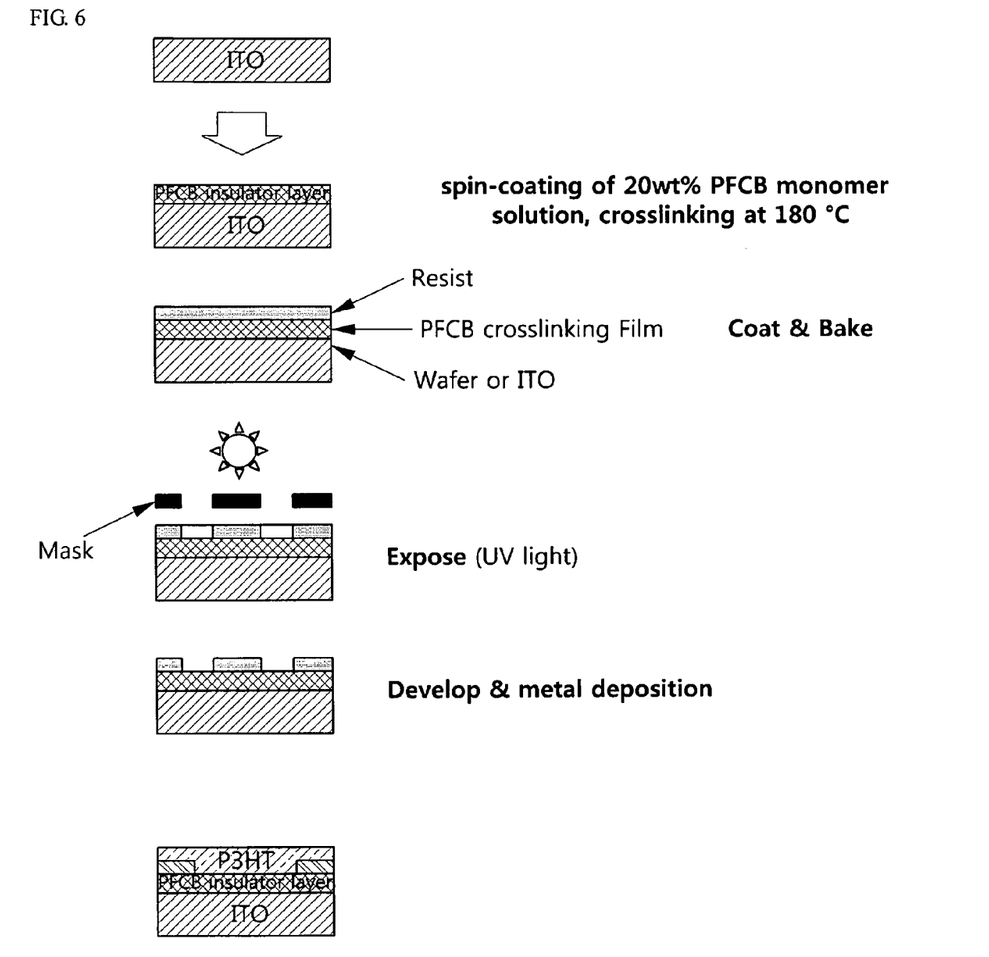
FIG. 6 is a flowchart illustrating an example of a method of manufacturing a bottom-contact organic thin-film transistor by forming electrodes on a gate insulating material, in which a polymer of Formula 2 prepared by polymerizing the compound represented by Formula 1 of the present invention is used, using a photolithography process.

First, a method of manufacturing a bottom-contact organic thin-film transistor will be described with reference to FIG. 6, which is a flowchart illustrating an example of the method of manufacturing a bottom-contact organic thin-film transistor by forming electrodes on a gate insulating material, in which the polymer of Formula 2 prepared by polymerizing the compound represented by Formula 1 of the present invention is used, using a photolithography process.

That is, a solution containing the perfluoroalkyleneoxy group-substituted phenylethylsilane compound of Formula 1 is coated on a substrate and dried and then heat-treated to form a gate insulating material layer. In this case, a silicon wafer substrate, an indium tin oxide (ITO) substrate, and the like may be used as the substrate. The compound of Formula 1 is dissolved in a solvent and coated to the substrate and then polymerized at a high temperature. The solvent may include tetrahydrofuran (THF), acetone, chloroform, dichloroethane, tetrachloroethane, cyclohexanone, and the like. Moreover, the coating process may include spin coating, dip coating, drop casting, doctor blade, and the like, to which an ordinary solution process can be applied. In case of conventional methods, it is difficult to perform a solution process since a lower layer may be damaged by the solution applied on an upper layer during the formation of a gate insulating material. However, the present invention can perform the solution process using the novel perfluoroalkyleneoxy group-substituted phenylethylsilane compound represented by Formula 1. After the coating process, the coated compound is thermally polymerized under vacuum conditions or in an inert gas atmosphere. The thermal polymerization may be performed in the temperature range from 150° C. to 250° C. for 1 to 3 hours (or until the point of time when the thermal polymerization is completed).

Next, a metal film for source/drain electrodes is patterned on the top of the gate insulating material layer and a coating material for ultraviolet-ray polymerization is applied thereon. Subsequently, ultraviolet rays are irradiated to form the source/drain electrodes.

The electrodes are formed using a photolithography process. More preferably, the source/drain electrodes are formed by a shadow mask to prevent current leakage.

Aurum used as the source/drain electrodes is patterned using a photolithography process in such a manner that a photopolymerization material (PR6612) for the photolithography process is coated and photopolymerized using ultraviolet light. The metal for electrodes is deposited on the source/drain electrodes and developed to form the electrodes. To form the electrodes using the photolithography process, the organic insulating material requires a high resistance to organic solvents and excellent mechanical properties. Existing organic insulating materials such as poly(vinylphenol), poly(styrene), polymethyl methacrylate, etc. have low insulation characteristics due to an increase in current leakage during the process. Moreover, the insulating polymers such as poly(imide) and the like, with which the photolithography process is readily performed, are hard to employ the solution process at low cost. Furthermore, since a heat treatment at a high temperature more than 300° C. is required, they are not suitable for the formation of elements that can be bent. The organic insulating material of the present invention can be coated using the solution process and, after the thermal polymerization, it is possible to form electrodes using a photolithography for a large-size substrate without an increase in current leakage.

The above-described metal may include aurum (Au), argentum (Ag), copper (Cu), chromium (Cr), platinum (Pt), etc. The solution in which the organic insulating material is dissolved is coated on the electrodes and heat-treated to form a semiconductor layer, thus manufacturing the bottom-contact organic thin-film transistor. The semiconductor layer is formed using organic semiconductor materials such as organic single molecules including pentacene, copper phthalocyanine (CuPc), sexithiophene, fullerene derivative, etc., and polymers such as thiophene polymer, poly(3-hexylthiophene), poly(9,9-dioctylfluorene-co-bithiophene), etc. That is, the organic semiconductor material is dissolved in chloroform, toluene, or chlorobenzene to be coated and then heat-treated to form the semiconductor layer.

The coating process of the organic semiconductor solution may be performed using spin coating, dip coating, drop casting, doctor blade, and the like in the temperature range from 80° C. to 150° C. for 10 to 60 minutes preferably (or until the point of time when the thermal polymerization is completed).

It is possible to manufacture a top-contact organic thin-film transistor in a manner similar to that of the bottom-contact organic thin-film transistor, except for the process of forming the insulating material layer on the semiconductor layer.

Figure 7:
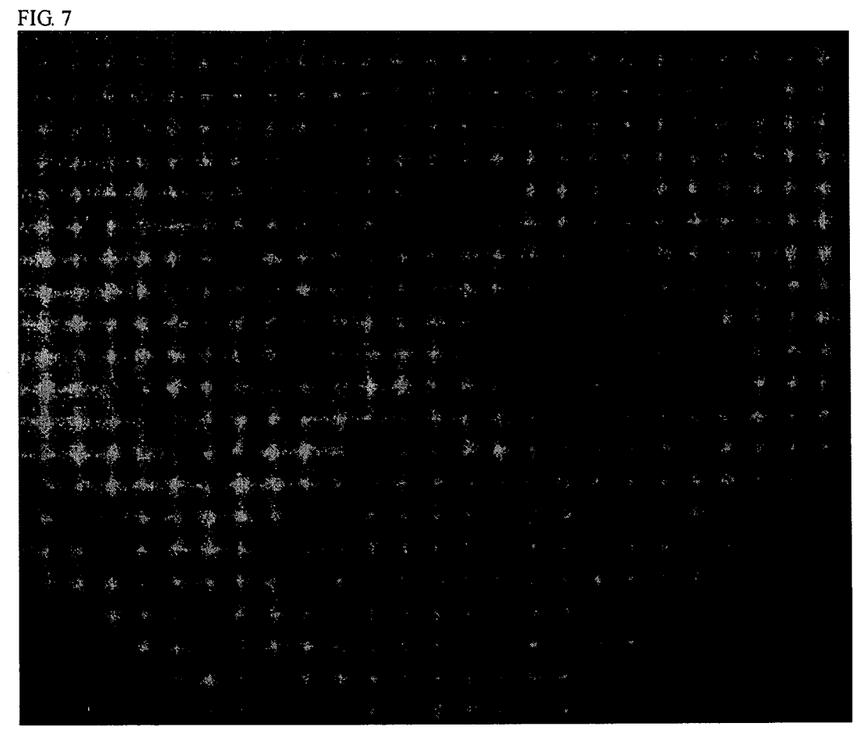
FIG. 7 is a photograph showing a bottom-contact organic thin-film transistor to which electrodes prepared using a photolithography process according to Example 2 of the present invention are applied.

A photograph of the bottom-contact organic thin-film transistor manufactured in the above-described method is shown in FIG. 7. It can be ascertained from the photograph that conductive electrodes are patterned neatly on the organic insulating material layer. Moreover, it can be found that the element manufactured using a transparent substrate can be employed as a transparent electrical element.

Figure 8:
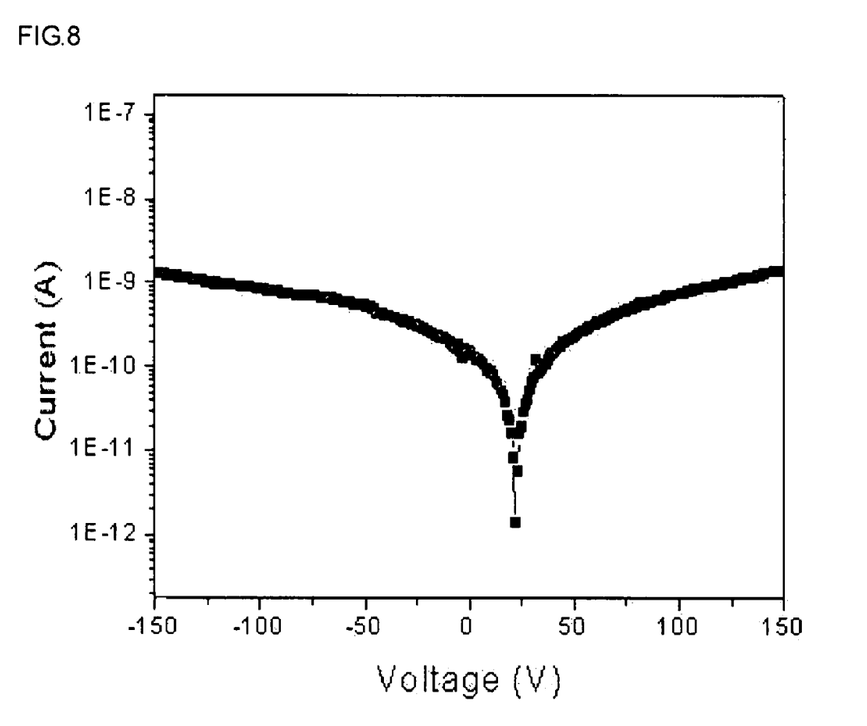
FIG. 8 is a graph showing electrical properties of an organic insulating layer prepared according to Example 2 of the present invention.
Figure 9:
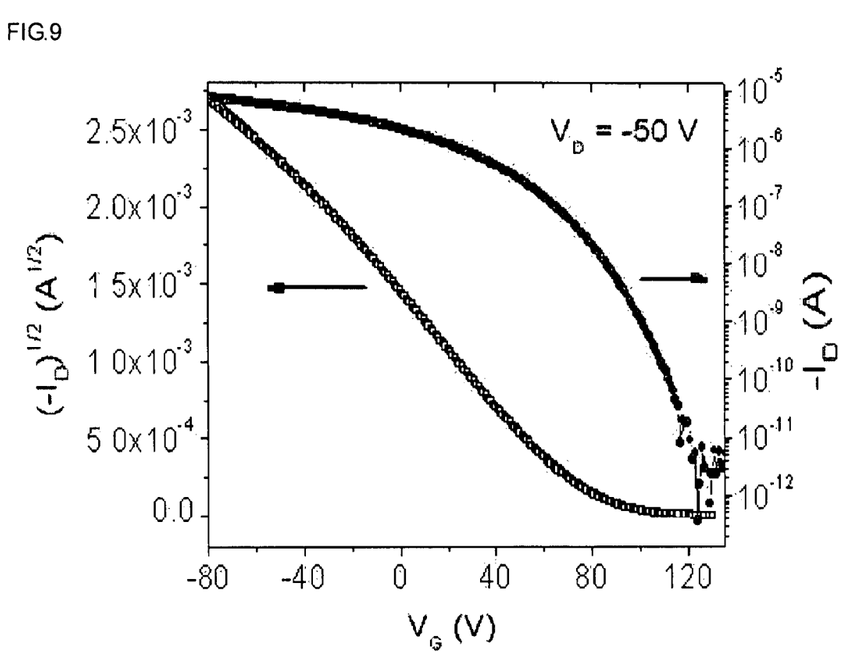
FIG. 9 is a graph showing electrical properties of a bottom-contact organic thin-film transistor prepared according to Example 2 of the present invention.

FIG. 8 is a graph showing electrical properties of the organic insulating layer prepared in accordance with the present invention, in which the electric current flows below $10^{-9}$ A and thereby it can be understood that its insulating effect is excellent. FIG. 9 is a graph showing electrical properties of the bottom-contact organic thin-film transistor prepared in accordance with the present invention, which shows excellent charge mobility of $1.8 \times 10^{-3}$ cm$^2$/Vs and on/off ratio of $8.3 \times 10^6$.

Hereinafter, the present invention will be described in more detail with reference to Examples; however, the present invention is not limited thereto.

EXAMPLE 1

Synthesis of Compound

An example of synthesizing a perfluoroalkyleneoxy group-substituted phenylethylsilane compound of Formula 1 and a polymer of Formula 2 prepared by polymerizing the same is shown in the following Scheme 1.

The synthesis was performed using a start material, 4-(trifluorovinyloxy)bromobenzene, commercially available from Oakwood Products, Inc., in a well known method (U.S. Pat. No. 5,066,746).

The reaction was performed in a low-temperature reactor at −78° C.

That is, 3 g (12 mmol) of trifluorovinyloxy bromobenzene was dissolved in 50 mL of diethylether and 7 mL (12 mmol) of 1.7M-butyllithium was added dropwise slowly to the solution under a nitrogen atmosphere. In general, a lithium-substituted trifluorovinyloxy bromobenzene has a reactivity with phenethyltrichlorosilane. After stirring the resulting solution for about 1 hour, 1 g (4 mmol) of phenethyltrichlorosilane was added and stirred. Then, the temperature was increased to room temperature. 50 mL of water was added to the resulting solution for layer separation. The aqueous layer was removed after separation, the remaining organic solvent was evaporated, and the crude product was purified by chromatography using a silica gel column to obtain a compound 1b (Yield 15%).

The compound 1b was an organic solvent having a solubility of more than 40 weight % to tetrahydrofuran (THF), acetone, chloroform and dichloroethane.

Figure 1:
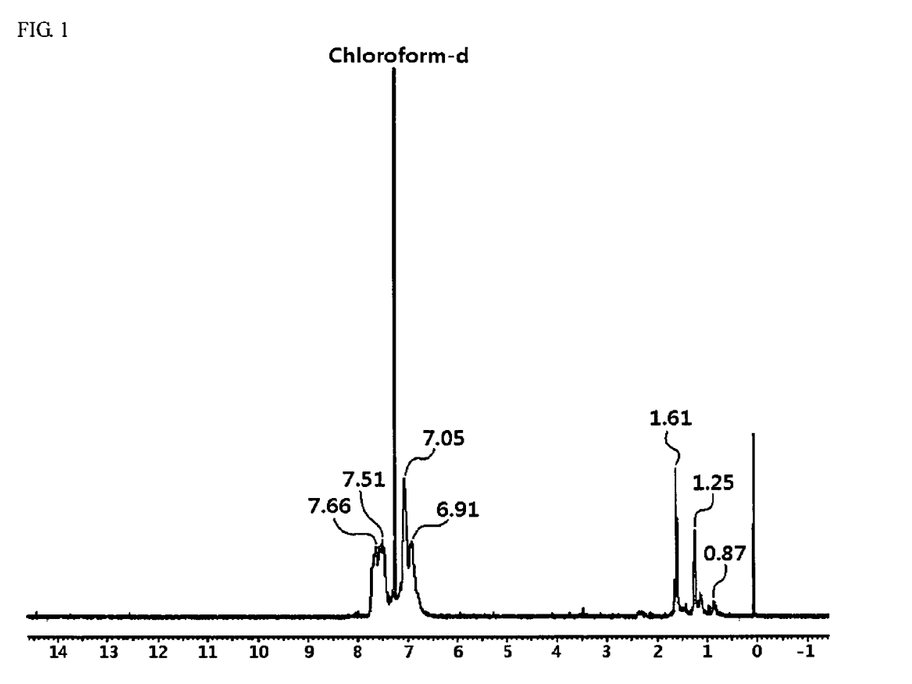
FIG. 1 shows a $^1$H-NMR spectrum of a compound of Formula 1a prepared according to Example 1 of the present invention.
Figure 2:
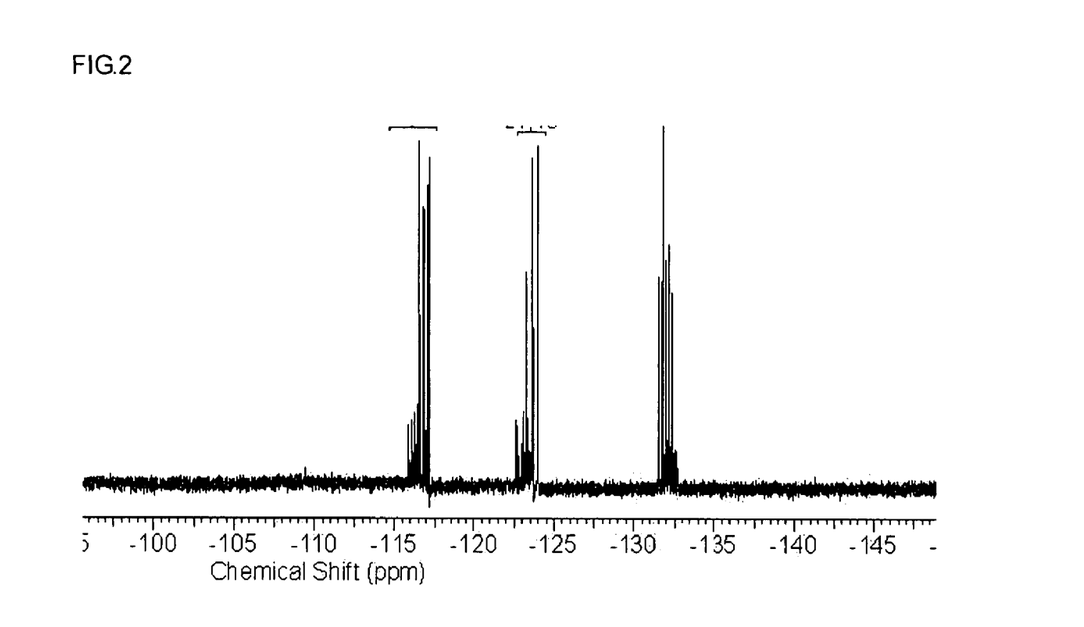
FIG. 2 shows a 19F-NMR spectrum of the compound of Formula 1a prepared according to Example 1 of the present invention.

The structure of the compound 1b was analyzed by $^1$H-NMR and $^{19}$F-NMR and the results are shown in FIGS. 1 and 2, respectively. In the above Scheme 1, if heat is applied to phenethylsilane containing a trifluorovinyl group, the trifluorovinyl group undergoes 2p+2p cyclodimerization and thereby the compound 1b is thermally crosslinked to form a polymer of Formula 2b.

Figure 3:
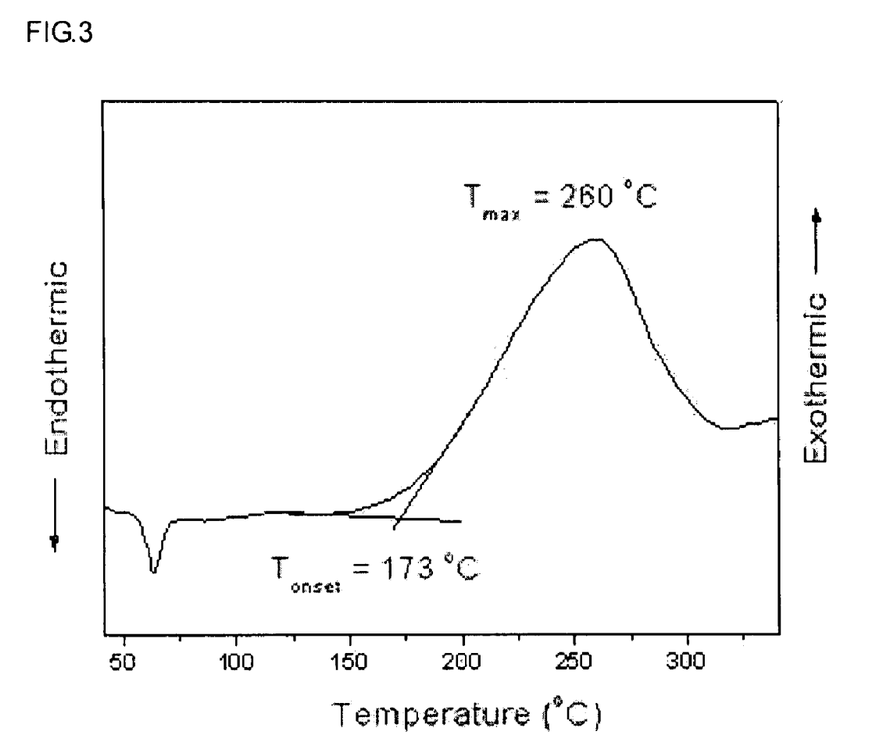
FIG. 3 is a graph showing results of a polymer of Formula 2b analyzed by differential scanning calorimeters, the polymer of Formula 2b being prepared by thermally polymerizing the compound of Formula 1b prepared according to Example 1 of the present invention.

FIG. 3 is a graph showing results of the polymer of Formula 2b prepared by thermal cyclodimerization of the compound of Formula 1b.

Figure 4:
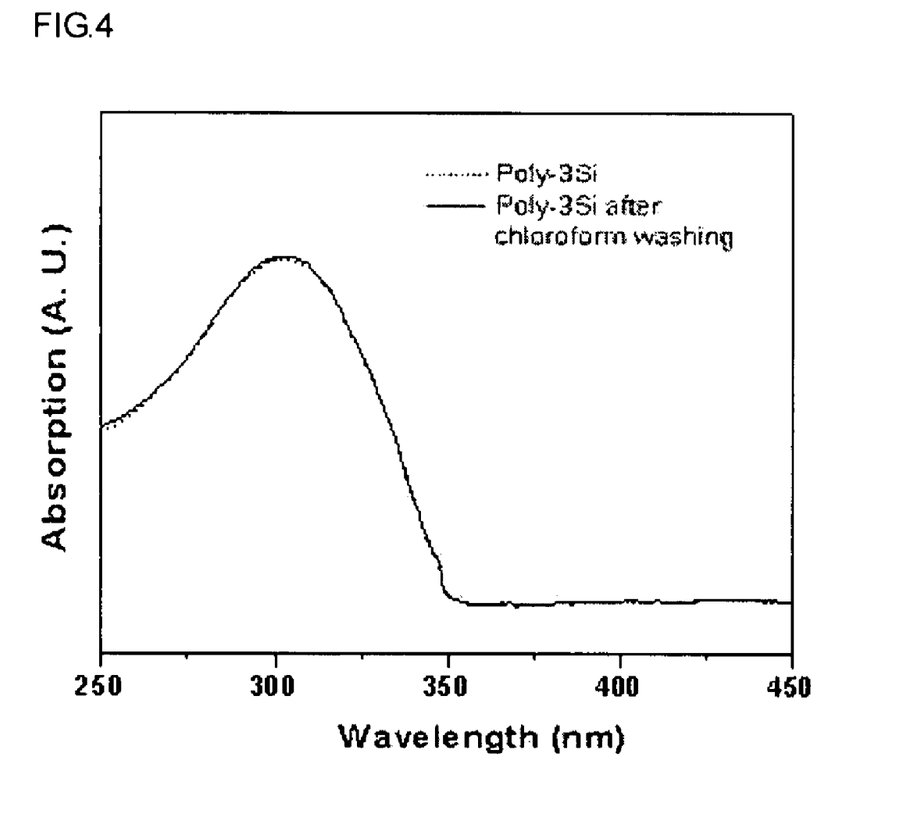
FIG. 4 shows a UV-Vis absorption spectrum of the thicknesses measured before and after washing an insulating film (layer), comprising the polymer of Formula 2b prepared by thermally polymerizing the compound of Formula 1b prepared according to Example 1 of the present invention, with an organic solvent.

FIG. 4 is a graph showing a resistance of the polymer of Formula 2b to an organic solvent, and it can be ascertained from the UV-Vis absorption spectrum that the thickness of the polymer film comprising the polymer of Formula 2 is not changed after washed with an organic solvent (chloroform).

Figure 5:
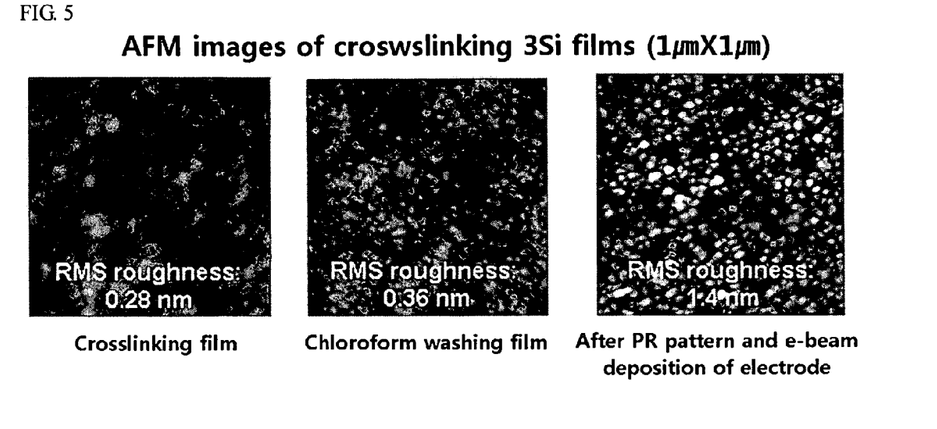
FIG. 5 is photographs, taken by atomic force microscopy (AFM), showing surface structures before and after washing an insulating film (layer), comprising the polymer of Formula 2b prepared by thermally polymerizing the compound of Formula 1b prepared according to Example 1 of the present invention, with an organic solvent.

FIG. 5 is photographs, taken by atomic force microscopy (AFM), showing that the surface structure of the polymer of Formula 2b is not changed after washed with the organic solvent.

EXAMPLE 2

Preparation of Organic Thin-Film Transistor

The monomer of Formula 1b prepared in accordance with Example 1 was dissolved in a tetrachloroethane solution at a concentration of about 20 weight % and spin-coated on a silicon or indium tin oxide (ITO) substrate at a rotational speed of 1,000 rpm for 60 seconds and then dried. Subsequently, the resulting solution was heated up to about 180° C. under a nitrogen atmosphere to be thermally crosslinked, thus preparing the polymer of Formula 2b.

Aurum used as the source/drain electrodes was patterned using a photolithography process in such a manner that a photopolymerization material (PR6612) for the photolithography process was coated and photopolymerized using ultraviolet light. The metal for electrodes was deposited on the source/drain electrodes using a deposition method such as e-beam or thermal deposition and then developed to form the electrodes.

The metal for electrodes was deposited under a vacuum of $10^{-6}$ Torr at 0.3 Å/s by an e-beam deposition process. At this time, a pattern having a length of 1 mm and a width of 5 μm was formed.

An organic semiconductor material, polyhexylthiophene, dissolved in chloroform at a concentration of 1 mg/ml was spin-coated on the pattern at a rotational speed of 2,000 rpm for 40 seconds and heated at a temperature of 120° C. for 10 minutes to increase the crystallinity.

EXPERIMENTAL EXAMPLE

Analysis of Semiconductor Properties

Properties of the organic field effect transistor (FET) prepared in accordance with Example 2 was analyzed using a Keithley 4200-SCS semiconductor parameter analyzer and the results are shown in FIG. 9.

According to FIG. 9, it can be ascertained that a semiconductor element having a high on/off ratio of more than $10^6$ was manufactured.

As described above, a perfluoroalkyleneoxy group-substituted phenylethylsilane compound proposed by the present invention has excellent thermal and chemical stability to be solution-processed in a monomer state, and a polymer prepared by thermally crosslinking the compound has also excellent thermal and chemical stability and thereby has a high resistance to organic solvents.

The present invention has advantages in that a solution process can be employed in forming films using the perfluoroalkyleneoxy group-substituted phenylethylsilane compound and the polymer thereof proposed by the present invention, and in coating semiconductor materials using the perfluoroalkyleneoxy group-substituted phenylethylsilane compound and the polymer thereof of the present invention as gate insulating materials. Moreover, the perfluoroalkyleneoxy group-substituted phenylethylsilane compound and the polymer thereof of the present invention can be effectively used when a flexible substrate is applied.

Since the perfluoroalkyleneoxy group-substituted phenylethylsilane compound and the polymer thereof of the present invention have excellent mechanical resistance, it is possible to introduce a patterning method using a photolithography for a large-size substrate in forming electrodes, thus enabling mass production in a simple process. Moreover, it is expected that the perfluoroalkyleneoxy group-substituted phenylethylsilane compound and the polymer thereof of the present invention will be used as essential materials for organic thin-film transistors required for disposable electronic products, radio frequency identification (RFID) tags, and the like in the coming ubiquitous society.

Furthermore, an organic thin-film transistor in which the perfluoroalkyleneoxy group-substituted phenylethylsilane compound and the polymer thereof of the present invention are introduced shows excellent on/off ratio.

As above, preferred embodiments of the present invention have been described and illustrated, however, the present invention is not limited thereto, rather, it should be understood that various modifications and variations of the present invention can be made thereto by those skilled in the art without departing from the spirit and the technical scope of the present invention as defined by the appended claims.

What is claimed is:

1. A perfluoroalkyleneoxy group-substituted phenylethylsilane compound represented by the following Formula 1:

[Formula 1]

wherein $R_1$, $R_2$ and $R_3$ are the same or different, independently selected from the group consisting of a $C_1$-$C_4$ alkyl group and a $C_1$-$C_4$ fluoroalkyl group substituted with 1 to 6 fluoro atoms, and at least one fluoro atom or fluoroalkyl group; $Z_1$, $Z_2$ and $Z_3$ are the same or different and independently selected from the group consisting of a hydrogen atom and a $C_1$-$C_4$ alkyl group; and n is 0, 1, 2 or 3.

2. The compound of claim 1, wherein at least one of the $R_1$, $R_2$ and $R_3$ is a fluoro atom.

3. The compound of claim 1, represented by the following Formula 1a:

[Formula 1a]

4. A perfluoropolymer prepared by polymerizing a perfluoroalkyleneoxy group-substituted phenylethylsilane compound represented by the following Formula 1:

[Formula 1]

wherein $R_1$, $R_2$, $R_3$, $Z_1$, $Z_2$, $Z_3$, and n are the same as defined above in claim 1.

5. A perfluoropolymer having a repeating unit structure represented by the following Formula 2:

[Formula 2]

wherein $R_1$, $R_2$, $R_3$, $Z_1$, $Z_2$, $Z_3$, and n are the same as defined above in claim 1.

6. The perfluoropolymer of claim 5, wherein the perfluoropolymer has a repeating unit structure represented by the following Formula 2a:

[Formula 2a]

7. An insulating layer comprising the perfluoropolymer of any one of claims 4 to 6.

8. A gate insulating material for an organic thin-film transistor comprising the perfluoropolymer of any one of claims 4 to 6.

9. An organic thin-film transistor comprising:
a substrate;
a gate insulating material layer formed on the substrate and comprising the perfluoropolymer of any one of claims of 4 to 6;
source/drain electrodes formed on the gate insulating material layer; and
a semiconductor layer formed on the gate insulating material layer and including a channel layer formed over the source/drain electrodes and therebetween.

10. An organic thin-film transistor comprising:
a substrate;
source/drain electrodes formed on the substrate;
a semiconductor layer formed on the substrate and including a channel layer formed over the source/drain electrodes and therebetween; and
a gate insulating material layer formed on the semiconductor layer and comprising the perfluoropolymer of any one of claims of 4 to 6.

* * * * *